(12) United States Patent
Langsdorf et al.

(10) Patent No.: US 9,107,805 B2
(45) Date of Patent: *Aug. 18, 2015

(54) PHARMACEUTICAL AND MEDICAL CONTAINER

(71) Applicant: Schott AG, Mainz (DE)

(72) Inventors: Andreas Langsdorf, Ingelheim (DE); Juergen Thuerk, St. Gallen (CH); Aurel Kunz, Appenzell (CH); Ulrich Lange, Mainz (DE); Joachim Kuester, Erzhausen (DE); Bernd Loeffelbein, Saulheim (DE); Marcus Meinefeld, Coppenbruegge (DE); Uwe Rothhaar, Birkenheide (DE); Axel Ohlinger, Wiesbaden (DE)

(73) Assignee: SCHOTT AG, Mainz (DE)

( * ) Notice: Subject to any disclaimer, the term of this patent is extended or adjusted under 35 U.S.C. 154(b) by 22 days.

This patent is subject to a terminal disclaimer.

(21) Appl. No.: 13/852,039

(22) Filed: Mar. 28, 2013

(65) Prior Publication Data

US 2013/0213849 A1    Aug. 22, 2013

Related U.S. Application Data

(62) Division of application No. 12/700,762, filed on Feb. 5, 2010, now Pat. No. 8,464,553.

(30) Foreign Application Priority Data

Feb. 6, 2009 (DE) .................. 10 2009 008 723
Dec. 22, 2009 (EP) .................. 09 180 471

(51) Int. Cl.
*B32B 1/02* (2006.01)
*A61J 1/05* (2006.01)
*A61M 5/31* (2006.01)
*C03B 9/193* (2006.01)
*A61J 1/00* (2006.01)

(52) U.S. Cl.
CPC .............. *A61J 1/05* (2013.01); *A61M 5/3129* (2013.01); *C03B 9/193* (2013.01); *C03B 9/1932* (2013.01); *A61J 1/00* (2013.01); *Y10T 428/131* (2015.01)

(58) Field of Classification Search
CPC .............. C03B 9/193; A61J 1/00; A61J 1/05; Y10T 428/131
USPC ........... 428/34.4, 426; 65/66, 68, 71, 72, 109, 65/302, 35
See application file for complete search history.

(56) References Cited

U.S. PATENT DOCUMENTS 3,171,729 A    3/1965  Andersen
5,149,474 A    9/1992  Rohatyn
6,415,631 B1   7/2002  Weston et al.
(Continued)

FOREIGN PATENT DOCUMENTS

DE   1 241 057   12/1967
GB     572984    11/1945

*Primary Examiner* — Walter B Aughenbaugh
(74) *Attorney, Agent, or Firm* — Harness, Dickey & Pierce, P.L.C.

(57) ABSTRACT

A container for pharmaceutical and medical applications made from glass, preferably from a borosilicate glass. The container is formed in the shape of a hollow body open at both its ends with a cylindrical portion having a wall thickness tolerance of maximally ±0.2 mm. The borosilicate glass has a nominal boron content that drops by less than 40% relative to the nominal value at all of the surfaces of the container.

15 Claims, 6 Drawing Sheets

(56) References Cited

U.S. PATENT DOCUMENTS 6,698,241 B1 3/2004 Schwarzer
8,158,225 B2 * 4/2012 Langsdorf et al. ........... 428/34.4
2005/0087213 A1 4/2005 Hahn

* cited by examiner

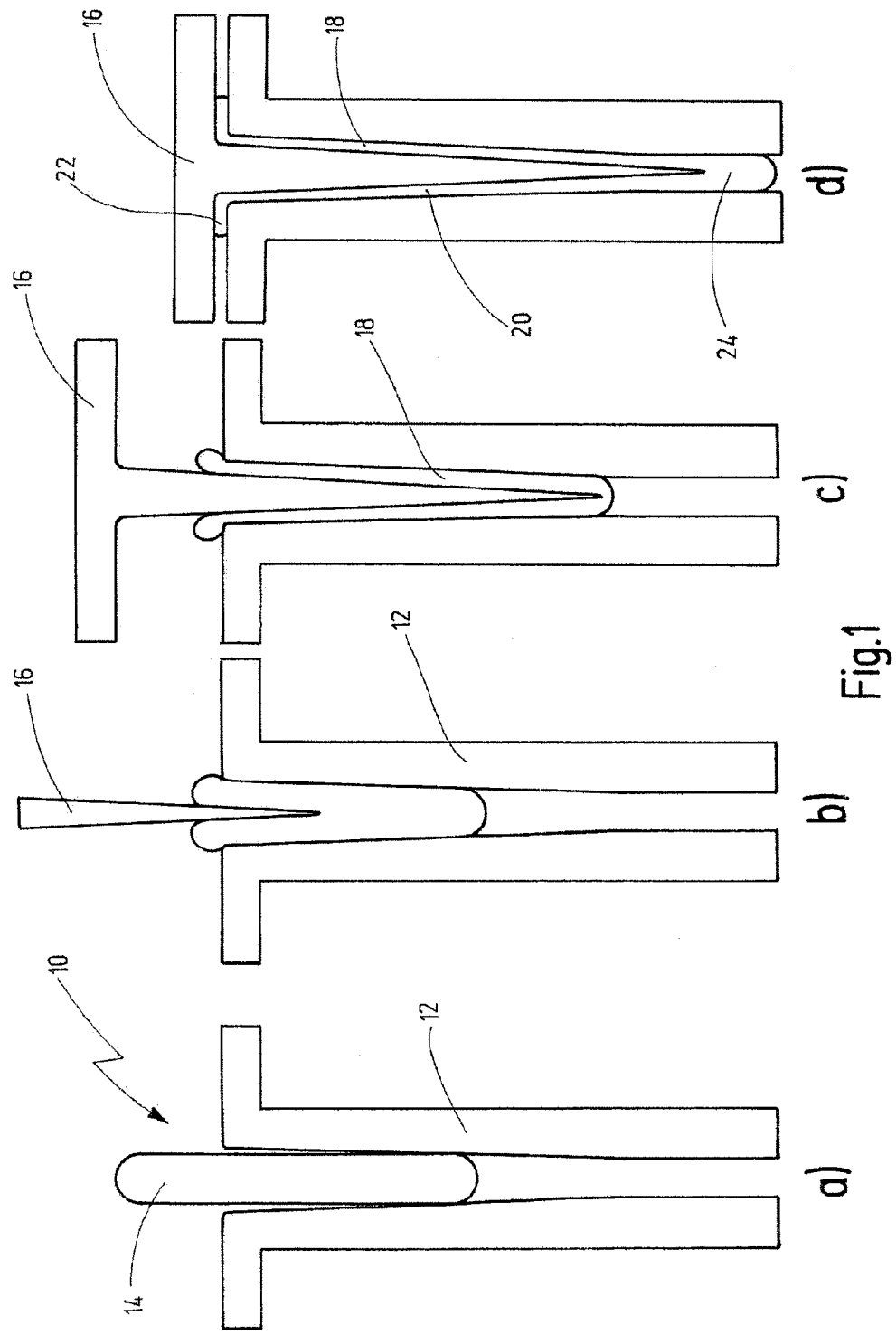

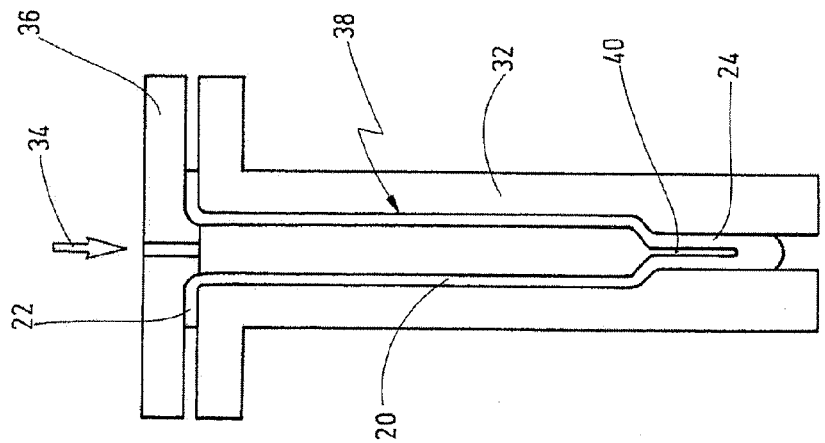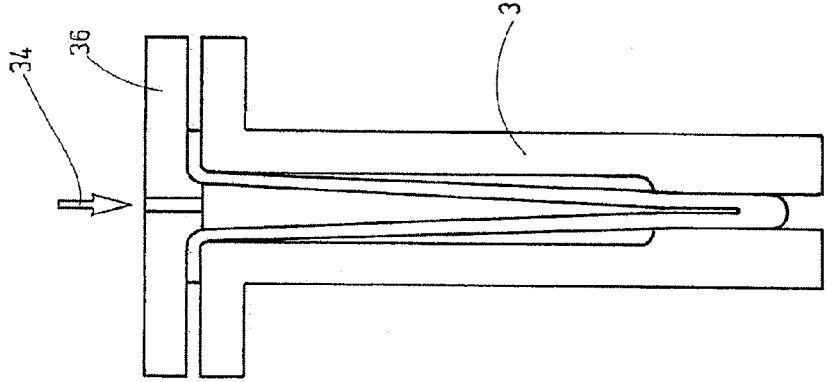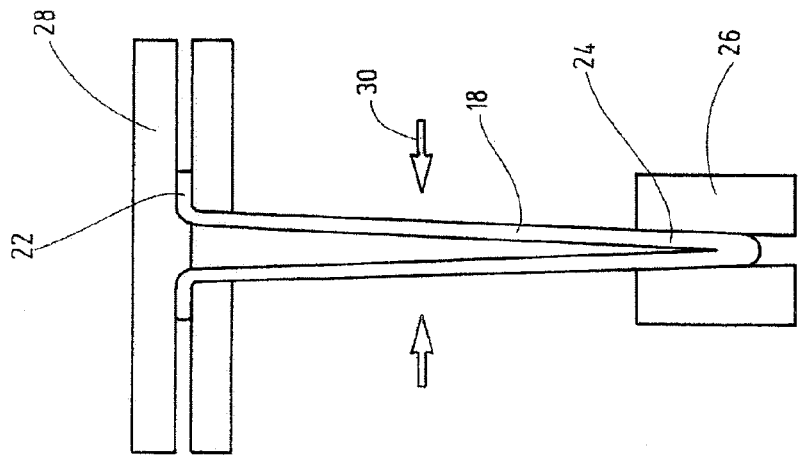

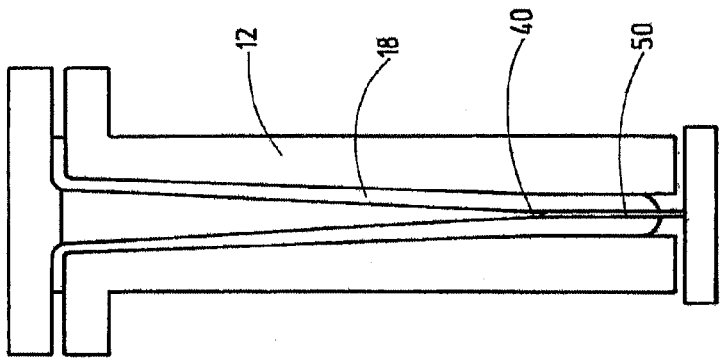
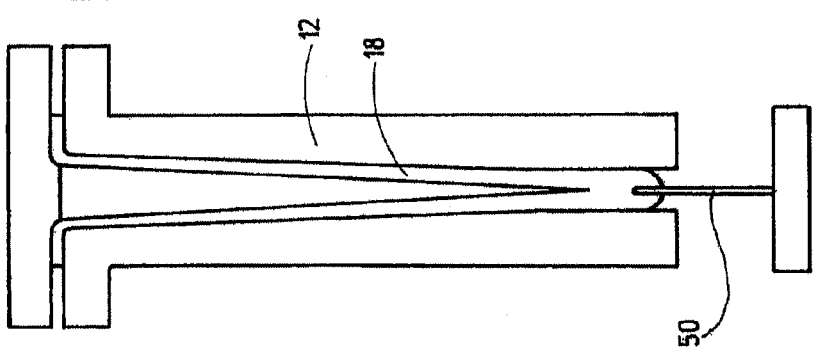
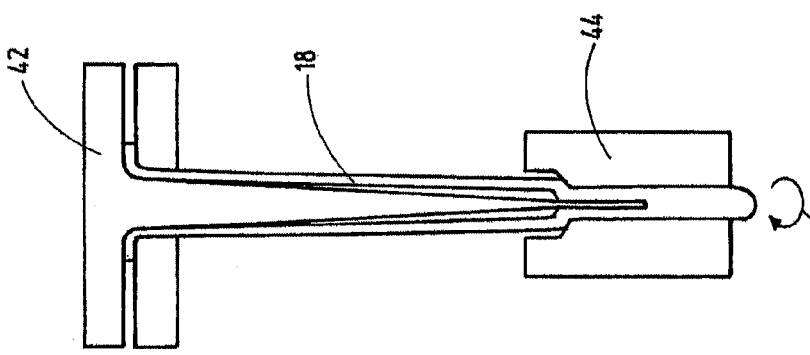
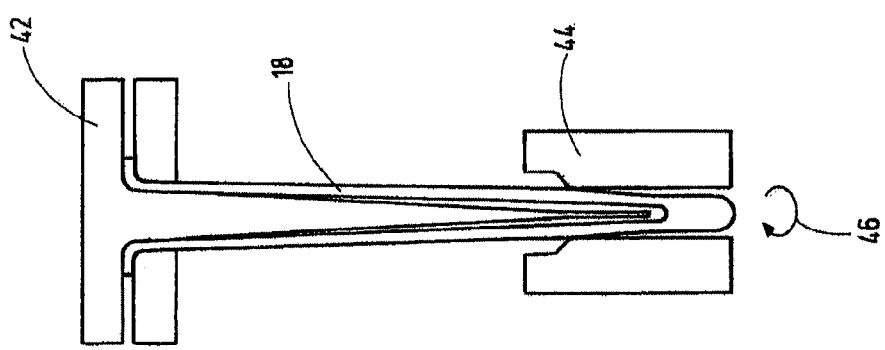

PHARMACEUTICAL AND MEDICAL CONTAINER

CROSS-REFERENCE TO RELATED APPLICATIONS

This application is a divisional of U.S. application Ser. No. 12/700,762, filed Feb. 5, 2010, now U.S. Pat. No. 8,464,553, claims priority to German Application No. 10 2009 008 723.0, filed Feb. 6, 2009 and to European Application No. 09 180 471.6, filed Dec. 22, 2009. The entire contents of these priority applications are incorporated herein by reference.

BACKGROUND OF THE INVENTION

The present invention relates to a process of producing a container from glass, in particular of a container the shape of a hollow body open on both ends, more particularly in the shape of a syringe barrel, which is in particular suited for pharmaceutical and medical applications.

Pharmaceutical containers normally are made from tubes or by blow forming directly from the melt. Due to lower variations in thickness, containers made from tubes can be made with thinner wall thicknesses and with close wall thickness tolerances. As a result of the wall thickness problem, containers in the form of syringe barrels for pharmaceutical or medical applications are produced exclusively from tubes.

GB 572 984 proposes to form a syringe with an at least closely toleranced wall thickness by blowing using a blowpipe, and snap back forming on a mandrel, but this is a process where more than 50% of the glass is lost and has to be discarded, so that this process hardly lends itself to industrialization.

DE 1 241 057 A further discloses a production process for ampoules for pharmaceutical and medical purposes directly from the melt, where the glass quantity required is initially drawn from the glass melt using a blowpipe and is then blown, with the blowpipe rotating, into a two-part mold that is applied from the outside. According to another method of producing ampoules directly from the glass bath, the bottom of the melt pan comprises an opening through which the liquid glass is pressed out by a plunger from the top toward the bottom. The glass drop is cut off by automatically operated shears and drops into a funnel-like recess where it is retained either by vacuum or by a ring placed on top of the drop. A hollow mandrel, which is introduced automatically, then blows up the parison to form a hollow body.

These and other variants of a production process for ampoules do not guarantee satisfactory thickness tolerances for production of syringe barrels.

Accordingly, a production process based on preformed glass tubes has become generally accepted in the art for the production of pharmaceutical containers in the form of syringe barrels.

The drawbacks of that method are relatively high production cost and the fact that local reheating of the glass tube during the reforming process will result in depletion of certain components due to evaporation. For example, containers made from glass tubes normally will be depleted of boron and sodium in different surface areas when the containers are produced from borosilicate glasses. In addition, intermediate packaging and transportation to the reforming station of the tubes used as a starting material require additional measures if undesirable contamination or damage to the tubes is to be prevented.

As a rule, so-called "Type I glasses", sometimes also described as "neutral glasses", are used for the production of pharmaceutical or medical containers of the kind of interest in the present case. The glasses in question, as a rule borosilicate glasses, have a Class I resistance to water according to DIN ISO 719 and a Class I resistance to acids according to DIN 12116.

SUMMARY OF THE INVENTION

In view of this it is an object of the present invention to provide a process for the production, directly from the glass melt, of containers for medical or pharmaceutical purposes that are open on both ends and which are suited for use especially as syringe barrels or carpoules and comply with the tolerances prescribed for such containers.

According to the invention this object is achieved by a press-blow process where a ram presses a dispensed glass drop down into a mold that is open at its bottom, and where the parison produced in that way is given its near-net shape form by a subsequent blowing step.

The object of the invention is perfectly achieved in this way.

For, it has been found that using a press-blow process it is possible to produce a container in the form of a hollow body for pharmaceutical or medical applications, which is open on both ends, directly from the melt and with sufficient dimensional accuracy.

This provides considerable cost advantages as the process does completely without any separate production of tubes and subsequent reheating.

That precise production is rendered possible especially due to the fact that contrary to the press-blow process known in the prior art a mold is used that is open at its bottom. This limits the pressures encountered and permits even very thin parisons to be pressed.

In addition, the container so produced shows no or only very little surface depletion of readily volatile elements, such as boron or sodium.

The container can be produced in different dimensions, as requested by the pharmaceutical industry. The container in question is a hollow body, open on both ends, preferably having a cylindrical shape for use especially as a syringe barrel or carpoule.

The container especially comprises a cylindrical portion with a flange at its one end and a cone on its other end.

The term "cone" as used in the present application is meant to describe a portion having a diameter smaller than that of the medium cylindrical portion. The form of the cone depends on the particular product. As a rule, the cone tapers toward its end, although it may also have thicker spots in that region.

As a rule, the container is produced with a full-length cone channel in its cone.

The cone channel may be opened already during the pressing step so that the final shape is reached. Otherwise after the pressing step the cone is cut at its outer end to open the cone channel.

The parison is given substantially the form of a hollow truncated cone in the pressing step.

Preferably, the parison has a wall thickness that tapers from the cone toward the flange in the cylindrical portion of the container.

It is possible in this way, in combination with the subsequent blowing step, to produce the cylindrical portion with close thickness tolerances.

According to another embodiment of the invention, the parison is heated in its medium portion, after the down stroke of the ram and prior to the subsequent blowing step, preferably to a temperature at which the glass has a viscosity of less than $10^{4.7}$ dPas.

Further, after the down stroke of the ram and prior to the blowing step that follows, the parison is cooled at least on one of its two ends, preferably to a temperature at which its viscosity is above $10^{10}$ dPas.

These features guarantee high-quality blow forming in the medium portion, while the two ends of the parison, i.e. the flange and the cone area, are not further reformed, being adequately cooled.

According to a further embodiment of the invention, the parison is preformed without a cone channel by a bigger ram in a first pressing step and the cone channel is then shaped using a second ram in a second pressing step.

The second pressing step may by carried out in that case from the side opposite the flange.

Alternatively, there may be provided a mandrel, being guided in the ram, by which the cone channel is produced by the down stroke of the ram after the glass volume supplied has been pressed out.

This feature provides a simple way of forming the cone channel.

According to still another embodiment of the invention, the glass drop is dispensed from a feeder and drops immediately into the mold. Dispensing in portions preferably is effected by a needle feeder without shears. Marks left by the shears are avoided in that case.

According to an alternative embodiment of the invention, the glass drop is dispensed from a feeder, drops onto the press mold and is then pressed into the press mold by the ram.

Both variants guarantee production with the desired dimensional accuracy.

According to a further variant of a process according to the invention, a parison is formed in a first pressing step, using a ram that is conical preferably over its full length which is replaced in a subsequent step by a mandrel having the desired shape of the cone channel, and the parison is then driven to rotate and is shaped by application of molding rolls in the region of the cone.

In that case, the parison is reheated once more, preferably in the region of the cone, before the molding rolls are applied.

These features allow a very high degree of dimensional accuracy of the container to be achieved, especially in the region of the cone.

According to a further embodiment of the invention, a vacuum is applied during the pressing step.

That feature assists the pressing operation and helps achieve the desired form and tolerance of the parison.

According to another embodiment of the invention, the cone is cut off at its outer end in order to open up the cone channel.

In case the cone channel cannot be opened up at its end already during the pressing operation, opening up of the cone channel at its end is achieved in this way by simple means.

A container for pharmaceutical and medical applications according to the invention, made from borosilicate glass, preferably from a Type I glass, comprises a cylindrical portion having a wall thickness tolerance of maximally ±0.2 mm, and the boron content of the container, at all its surfaces, drops by less than 60%, preferably less than 40%, more preferably less than 20% relative to its nominal value.

Due to its production directly from the melt, without any use of preformed tubes, the container according to the invention has a more homogeneous glass composition over its entire extension.

Similarly, the sodium content of the container, at all its surfaces, drops by less than 30%, preferably less than 20%, relative to its nominal value.

The container may have the most different dimensions, as requested by the pharmaceutical industry, and may in particular comprise a flange on its one end and a cone on its other end.

According to the invention, the container according to the invention, being produced directly from the melt, may also be produced in very small dimensions and may contain a total glass mass of maximally 15 g, especially maximally 10 g, especially maximally 5 g.

Correspondingly, the volume of the container may be maximally 15 ml, especially maximally 10 ml, especially maximally 5 ml.

Further, the container may have an overall height and an overall diameter such that the overall height can be equal to at least 1.5 times the value of the overall diameter.

Finally, the container may also have a very small wall thickness of <1.5 mm, especially <1.3 mm, or even <1.1 mm.

Still, the wall thickness tolerance may be ≤±0.2 mm or even ≤±0.1 mm.

It is understood that the features of the invention mentioned above and those yet to be explained below can be used not only in the respective combination indicated, but also in other combinations or in isolation, without leaving the scope of the invention.

BRIEF DESCRIPTION OF THE DRAWINGS

Further features and advantages of the invention will become apparent from the description that follows of preferred embodiments, with reference to the drawing. In the drawing:

FIGS. 1a)-d) show different phases of the pressing process for the production of a parison directly from the melt, where the melt it pressed through a press mold that is open at its bottom;

FIG. 2 shows a diagrammatic representation of a step that follows the pressing operation illustrated in FIG. 1, for reheating the parison in its medium portion and for simultaneously cooling it at its two ends;

FIGS. 3a), b) show a blowing step, following the intermediate step illustrated in FIG. 2, in the initial phase and in the final phase, in which the preformed parison is blown to the final shape of the container in a blowing mold;

FIGS. 6a), b) show a further variant of the invention, where the pressing step is followed by a cone-shaping operation during which the parison is driven to rotate and molding rolls are applied for shaping the parison in its cone region;

FIGS. 7a), b) show a further variant of a pressing process according to the invention, where the cone channel is formed by a ram from the cone end in a second pressing operation, following the first pressing operation.

DETAILED DESCRIPTION OF THE PREFERRED EMBODIMENTS

Figure 4:
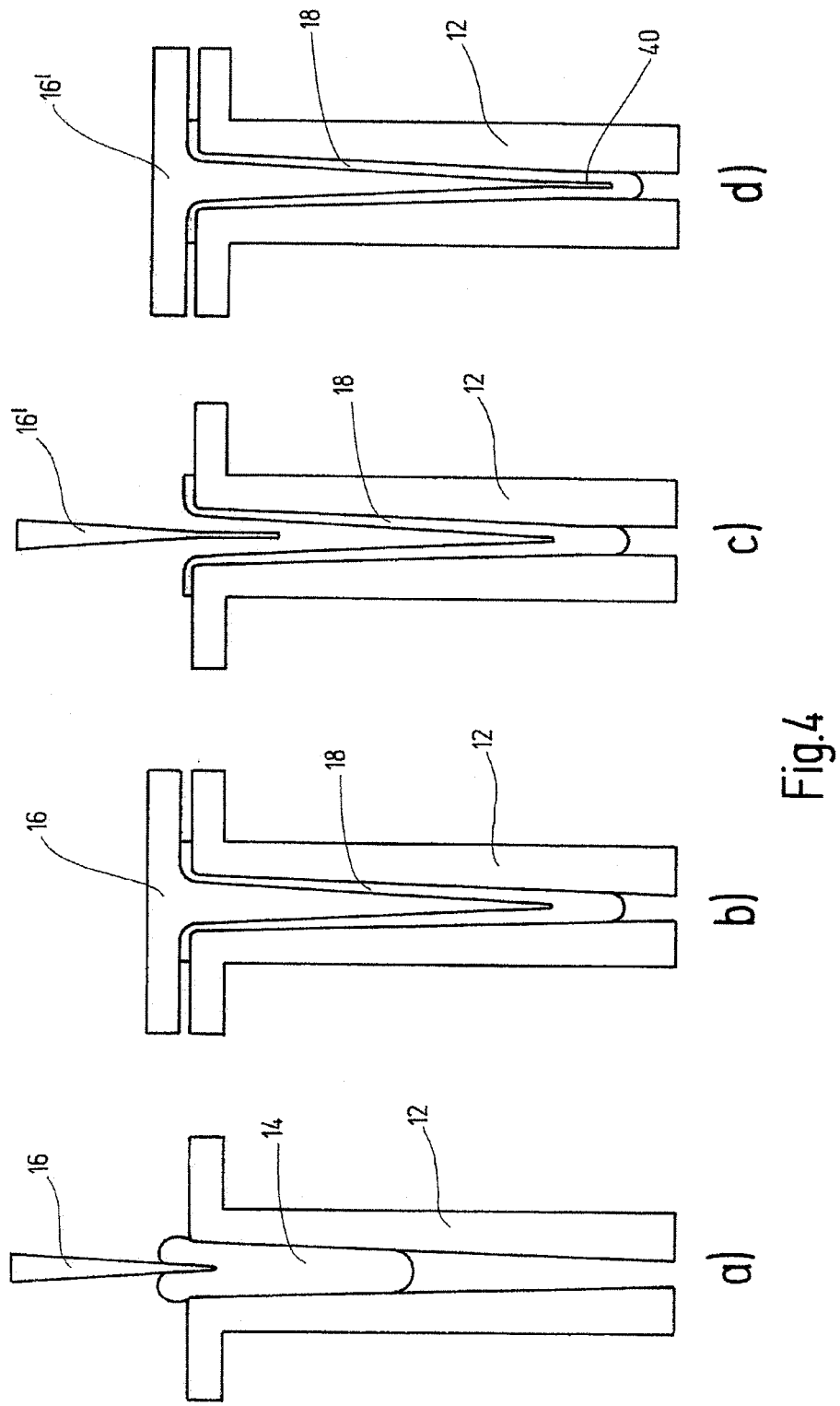
FIGS. 4a)-d) show different phases of an alternative pressing operation, with a pre-pressing step using a first ram and an after-pressing step using a second ram, by which the desired final shape of the cone channel is finally produced.

FIG. 1 shows a pressing device for pressing a parison 18 directly from a drop from the melt, indicated generally by reference numeral 10. A drop 14 is dispensed from a needle feeder without shears, and drops directly into a mold 12 (FIG. 1a). In a next step, shown in FIG. 1b), a ram 16 performs a downward stroke and begins to form a parison from the drop 14 by a pressing step. As can be seen in FIG. 1c), a big part of the parison 18 has already been pressed into the mold 12 and, as can be seen in FIG. 1d), the parison has its final form already after completion of the pressing step.

In the illustrated case, a container having a cylindrical medium portion is to be produced, with an integrally formed flange on its one end and a cone, which has a diameter smaller than the diameter of the cylindrical portion and which is passed by a full-length cone channel, on its other end.

At the end of the pressing operation, the parison 18, i.e. the preformed glass body, has a substantially conical shape with a medium portion 20, a flange 22 on its one end and a cone 24 on its other end.

The cone channel 40 does not have its final shape at the end of the pressing operation, as shown in FIG. 1d).

The pressing operation is followed by a shaping step consisting of a blowing process by which the parison 18 is given the final shape of the container 38, as illustrated in FIG. 3a), b).

Given, however, that no deformation, or practically no deformation, should occur during the blowing process in the area of the flange 22 of the container 38, nor in the area of its cone 24, one preferably performs an intermediate operation before the blowing operation according to FIG. 2, in which the parison 18 is reheated in its medium portion using a burner 30, while the area of the flange 22 of the parison, and the area of its cone 24, are cooled using a cooler 28 and/or 26.

Following that intermediate step according to FIG. 2, the parison 18 is transferred to a blowing mold 32 the inner contour of which conforms with the final shape of the finished container 38 according to FIG. 3. The parison 18 is fixed on the flange end by a dolly 36 which comprises a passage through which a fluid, for example air or nitrogen, can be blown in, as indicated by numeral 34. While the beginning of the pressing operation is illustrated in FIG. 3a), FIG. 3b) shows the end of the pressing operation, where the parison 18 has assumed the final form of the container 38, with a medium cylindrical portion 20, a flange 22 on its one end and a cone 24 on its other end. The cone channel 40, which begins inside the cylindrical portion 20, has not yet reached the outside and ends a short way before its outer end.

For opening up the cone channel 40, the container 38 is cut off at its cone 34 in a subsequent step so that the cone channel 40 then opens to the outside.

In the following, different process variants of the press-blow process for the production of a container directly from the melt, which have been described before with reference to FIGS. 1 to 3, will be explained in more detail with reference to FIGS. 4 to 7.

FIG. 4 shows one variant of a pressing step where two different rams 16, 16' are employed one after the other, instead of a single ram as shown in FIG. 1.

Using the first ram 16, the parison 18 is pre-pressed in an exclusively conical mold 12 (compare FIG. 4 a), b)), while a second ram 16' is used to press the parison once more in a second step. The first ram 16 has a purely conical shape, while the lower end of the second ram 16' is provided with a slim extension of the shape the cone channel will have later. Accordingly, the second ram 16' can shape the cone channel in the second pressing step with a short contact time, although the cone channel 40 had not been shaped at all in the first pressing step—see FIG. 4 a), b). That two-step process reduces the thermal loading on the ram and leads to shorter contact times.

Further processing of the parison 18 then occurs by a subsequent blowing step and/or intermediate step, as has been described above with reference to FIGS. 2 and 3.

Figure 5:
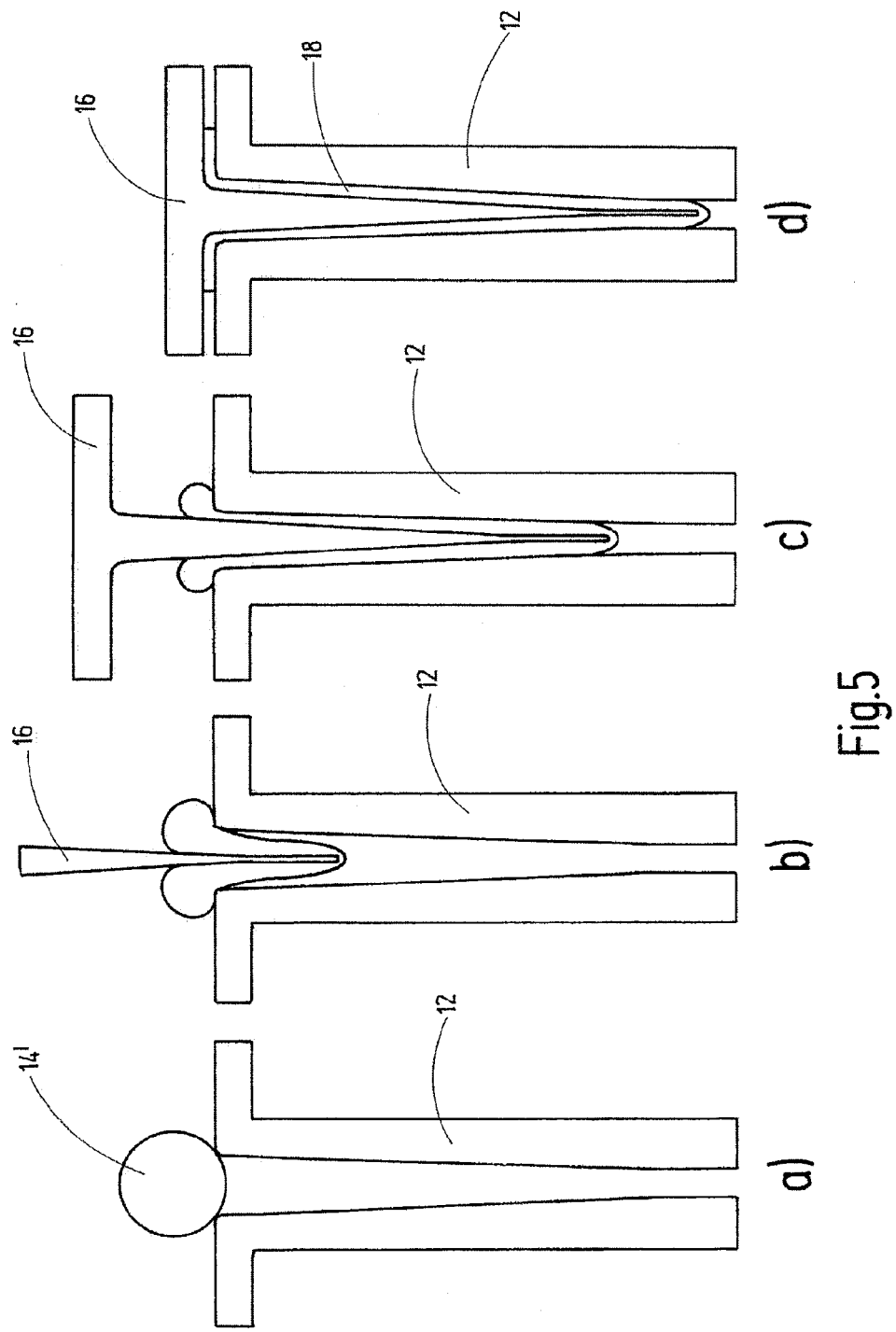
FIGS. 5a)-d) show a further alternative of the pressing operation according to the invention in different phases, where the embodiment according to FIG. 1 is modified so that the dispensed glass drop does not drop into the press mold immediately, but remains initially seated on the surface of the press mold and is then pressed into the press mold by the ram.

Another process variant is illustrated in FIG. 5. In that case, the drop, having been dispensed by a feeder, does not drop directly into the mold 12, which is open at its bottom, but falls initially onto the upper end of the mold 12, as indicated by the drop 14' (shown in FIG. 5a). It is only in the subsequent pressing step according to FIGS. 5b), c) and d) that the parison 18 is finally shaped. The glass drop 14' is then shaped by a down stroke of the ram 16 into the mold 12 so that it finally assumes its final shape shown in FIG. 5d).

Another process variant is illustrated in FIGS. 6a), 6b). In that case, the parison 18 is initially produced by pressing, as has been described above with reference to FIGS. 1a) to 1d). After having formed the parison 18, the ram is retracted and is replaced by a mandrel 42 whose shape conforms to the desired final shape of the parison 18, with the cone channel 40 integrally formed on its lower end. The parison 18 now is set to rotate, as indicated by arrow 46, and molding rolls 44 are progressively applied to bring the cone into its desired final shape illustrated in FIG. 6b).

Another process variant is illustrated in FIGS. 7a), b).

In that case, the parison 18 initially is produced by pressing, as has been explained above with reference to FIGS. 1a) to d). In a subsequent second process step, a second ram 50 then pierces the cone channel on the cone end so that the final form of the cone channel 40, open to the outside, is obtained without the need to cut off the container 38 later in order to open up the cone channel 40.

Example

Figure 8:
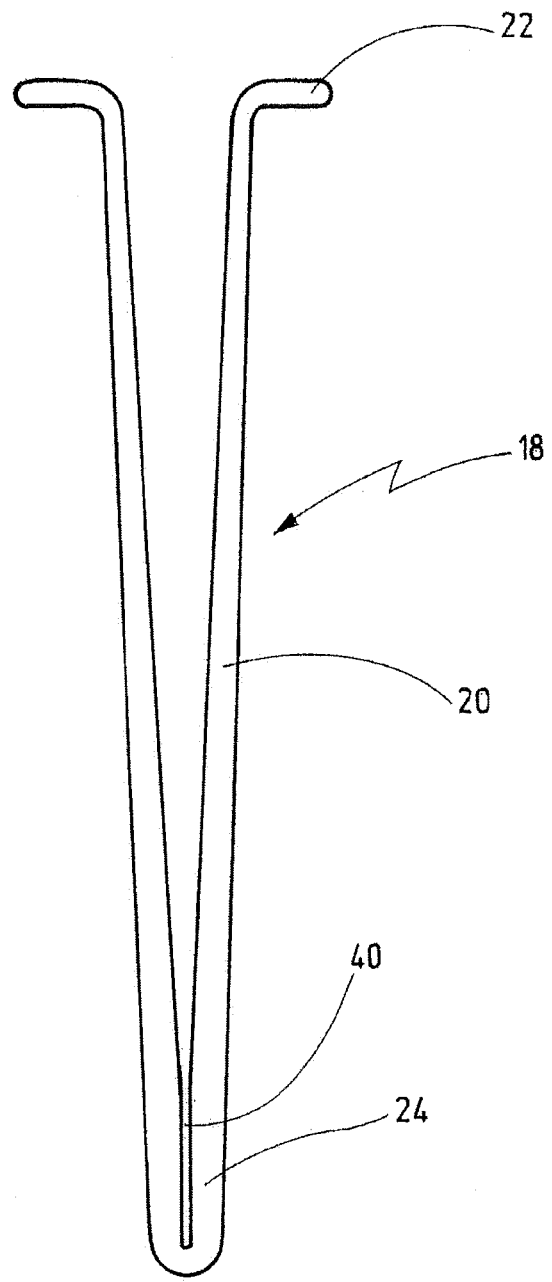
FIG. 8 shows an enlarged view of a molded parison in its preferred configuration, after the pressing step, from which it appears that after the pressing step the parison shows a wall thickness that tapers from the cone toward the flange in its medium are, i.e. that area which later becomes the cylindrical portion of the container.

A syringe barrel 38 is produced from FIOLAX®, a borosilicate glass produced and marketed by Applicant. The characteristics of the FIOLAX® glass used are summarized in Table 1. The syringe barrel 38 produced has a standard volume of 1 ml, a diameter in the cylindrical portion of 8.15 mm and an overall length of 64 mm, with a wall thickness of 0.9 mm in the region of the cylindrical portion. After a glass drop 14 has been dispensed by a needle feeder without shears, the glass drop 14 directly drops into the mold 12 shown in FIG. 1a). In the pressing step shown in FIGS. 1b) to d), the parison 18 is then pressed to a shape where the wall thickness in the region of the cylindrical portion 20 tapers from the cone 24 toward the flange 22, as can be clearly seen in the enlarged representation of FIG. 8.

TABLE 1

FIOLAX ® Data

| Chemical composition (Main components in % by weight) | | | | |
|---|---|---|---|---|
| SiO$_2$ | B$_2$O$_3$ | Al$_2$O$_3$ | Na$_2$O | CaO |
| 75 | 10.5 | 5 | 7 | 1.5 |

| Resistance to water | |
|---|---|
| According to DIN ISO 719 | Class HGB 1 |

| Resistance to acids | |
|---|---|
| According to DIN 12116 | Class S1 |

| Coefficient of thermal expansion | |
|---|---|
| α (20° C.) | 4.9 · 10$^{-6}$/K |
| Transformation temperature T$_g$ | 565° C. |

| Temperature of the glass at the viscosities η (in dPa · s) | |
|---|---|
| 10$^{13}$ (Upper cooling temperature) | 565° C. |
| 10$^{7.6}$ (Softening temperature) | 785° C. |
| 10$^4$ (Processing temperature) | 1165° C. |
| Density at 25° C. | 2,340 Kgs/m$^3$ |

According to FIG. 2, the parison 18 is then subjected to thermal intermediate conditioning, by reheating it locally in its cylindrical portion 20 using a burner and contact cooling of the flange 22 and the cone 24. During that process, the parison 18 is cooled down at its flange 22 and its cone 24 to a temperature of <650° C., preferably to approximately 600° C., while at the same time the cylindrical portion 20 is heated up to more than 1050° C., preferably to approximately 1200° C. The transition area between the high temperature in the cylindrical portion 20 and the low temperature in the flange 22 and the cone 24 is less than 10 mm.

Following that thermal intermediate conditioning, the parison 18 is then transferred into a blow mold according to FIG. 3a) and is closed at its flange end by means of a dolly 36. There then follows the blow-forming step at an overpressure of approximately 0.5 bar, at a temperature of over 1050° C. in the medium portion 20.

The syringe barrel 38 so produced is within its desired geometric specifications and especially has a wall thickness of 0.9 mm±100 μm in its medium cylindrical portion 20.

What is claimed is:

1. A container for pharmaceutical and medical applications made from a borosilicate glass melt with a first percentage by weight boron content, the container having the shape of a hollow body that is open on both of its ends, with the hollow body comprising a cylindrical portion having a substantially uniform wall thickness that varies by no more than ±0.2 mm, wherein actual boron content at any surface of the container diminishes by less than 40% relative to said first percentage by weight.

2. The container of claim 1, wherein the borosilicate glass melt has a second percentage by weight sodium content, and wherein actual sodium content at any surface of the container diminishes by less than 20%, relative to said second percentage by weight.

3. The container of claim 1, having a flange on its one end and a cone area on its other end that has a diameter smaller than the diameter of the cylindrical portion.

4. The container of claim 1, wherein the actual boron content at any surface of the container diminishes by less than 20% relative to said first percentage by weight.

5. The container of claim 1, having a total glass mass of maximally 15 g.

6. The container of claim 2, having a total glass mass of maximally 10 g.

7. The container of claim 1, having a total glass mass of maximally 5 g.

8. The container of claim 1, wherein said hollow body has the shape of a cylindrical barrel made from a Type I borosilicate glass.

9. The container of claim 1, having a volume of maximally 15 ml.

10. The container of claim 5, having a volume of maximally 10 ml.

11. The container of claim 5, having a volume of maximally 5 ml.

12. The container of claim 1, having an overall height and an overall diameter, where the overall height is equal to at least 1.5 times the value of the overall diameter.

13. The container of claim 1, having a wall thickness in said cylindrical portion that is smaller than 1.5 mm.

14. The container of claim 1, having a wall thickness in said cylindrical portion that is smaller than 1.3 mm.

15. The container of claim 1, having a wall thickness in said cylindrical portion that is smaller than 1.1 mm.

* * * * *